(12) United States Patent
Barry et al.

(10) Patent No.: US 9,891,196 B2
(45) Date of Patent: Feb. 13, 2018

(54) ULTRASONIC INSPECTION OF COMPOSITE PARTS

(71) Applicant: Bell Helicopter Textron Inc., Fort Worth, TX (US)

(72) Inventors: Robert J. Barry, Arlington, TX (US); Jeffrey P. Nissen, Fort Worth, TX (US); Edward Hohman, Mansfield, TX (US)

(73) Assignee: BELL HELICOPTER TEXTRON INC., Fort Worth, TX (US)

( * ) Notice: Subject to any disclaimer, the term of this patent is extended or adjusted under 35 U.S.C. 154(b) by 155 days.

(21) Appl. No.: 14/476,091

(22) Filed: Sep. 3, 2014

(65) Prior Publication Data

US 2016/0061779 A1   Mar. 3, 2016

(51) Int. Cl.
| | |
|---|---|
| *G01N 29/24* | (2006.01) |
| *G01N 29/04* | (2006.01) |
| *G01M 13/00* | (2006.01) |
| *G01N 29/22* | (2006.01) |
| *G01N 29/34* | (2006.01) |

(52) U.S. Cl.
CPC ............ *G01N 29/04* (2013.01); *G01M 13/00* (2013.01); *G01N 29/221* (2013.01); *G01N 29/225* (2013.01); *G01N 29/24* (2013.01); *G01N 29/341* (2013.01); *G01N 2291/023* (2013.01); *G01N 2291/0231* (2013.01); *G01N 2291/0289* (2013.01); *G01N 2291/106* (2013.01); *G01N 2291/2638* (2013.01); *G01N 2291/2694* (2013.01)

(58) Field of Classification Search
CPC ... G01N 2291/2694; G01N 2291/2638; G01N 2291/0231

USPC .......... 73/620, 625, 627, 628, 633, 636, 641
See application file for complete search history.

(56) References Cited

U.S. PATENT DOCUMENTS

| | | | | |
|---|---|---|---|---|
| 4,848,159 A | * | 7/1989 | Kennedy | .............. G01N 29/265 73/588 |
| 5,932,807 A | * | 8/1999 | Mallart | ................. B06B 1/0633 73/628 |
| 6,167,760 B1 | * | 1/2001 | Brunty | ............... G01N 29/0645 73/634 |
| 2006/0162456 A1 | * | 7/2006 | Kennedy | .............. G01N 29/225 73/620 |

(Continued)

FOREIGN PATENT DOCUMENTS

FR         2997190         4/2014

OTHER PUBLICATIONS

European Search Report issued in European Application No. 14189245.5 dated Jan. 8, 2015; 4 pages.

(Continued)

*Primary Examiner* — Manish S Shah
*Assistant Examiner* — Suman K Nath

(57) ABSTRACT

One aspect of a process to inspect a composite component includes traversing multiple ultrasonic probe array portions on respective multiple component surfaces of the composite component. The multiple component surfaces are either separate from or at angles to each other. The process includes simultaneously passing an ultrasonic signal into the multiple component surfaces through the multiple ultrasonic probe array portions. The process also includes receiving a response to the ultrasonic signal through the multiple ultrasonic probe array portions.

17 Claims, 5 Drawing Sheets

(56) References Cited

U.S. PATENT DOCUMENTS

| | | | |
|---|---|---|---|
| 2007/0044562 A1* | 3/2007 | Sarr | G01N 29/225 |
| | | | 73/618 |
| 2007/0044563 A1 | 3/2007 | Sarr et al. | |
| 2013/0233082 A1 | 9/2013 | Bond-Thorley et al. | |
| 2015/0053015 A1* | 2/2015 | Sarr | G01N 29/24 |
| | | | 73/632 |

OTHER PUBLICATIONS

Communication Pursuant to Article 94(3) EPC issued in European Application No. 14189245.5 dated Jul. 9, 2015; 5 pages.
Communication Pursuant to Article 94(3) EPC issued in European Application No. 14189245.5 dated Jul. 27, 2016; 6 pages.
Office action issued in Canadian Application No. 2,901,854 dated Jul. 26, 2016, 3 pages.

* cited by examiner

ULTRASONIC INSPECTION OF COMPOSITE PARTS

TECHNICAL FIELD

This disclosure relates to the ultrasonic inspection of parts, e.g., composite components for an aircraft.

BACKGROUND

In many industries, components are inspected for defects before installation. The components can be inspected using ultrasonic techniques. For example, composite components for use in an aircraft can be inspected for defects using an ultrasonic probe. Some components are large or have multiple surfaces that can increase the amount of time needed for a thorough ultrasonic inspection.

SUMMARY

This disclosure describes technologies relating to inspecting components with ultrasonic techniques.

Certain aspects of the subject matter described here can be implemented as a method to inspect a composite component. The method includes traversing multiple ultrasonic probe array portions on respective multiple component surfaces of the composite component, wherein the multiple component surfaces are either separate from or at angles to each other. The method includes simultaneously passing an ultrasonic signal into the multiple component surfaces through the multiple ultrasonic probe array portions. The method also includes receiving a response to the ultrasonic signal through the multiple ultrasonic probe array portions.

This, and other aspects, can include one or more of the following features. Simultaneously passing the ultrasonic signal into the multiple component surfaces through the multiple ultrasonic probe array portions can include dividing the ultrasonic signal into multiple ultrasonic signal portions and transmitting the ultrasonic signal portions to the multiple ultrasonic probe array portions. Receiving the response to the ultrasonic signal through the multiple ultrasonic probe array portions can include receiving multiple response signals to the respective multiple ultrasonic signal portions at the multiple component surfaces, each response signal received from a respective composite component surface in response to a respective ultrasonic signal portion. Receiving the response to the ultrasonic signal through the multiple ultrasonic probe array portions can also include aggregating the multiple response signals to form the response to the ultrasonic signal. Each ultrasonic probe array portion can include multiple ultrasonic probes. The multiple ultrasonic probes can be arranged in at least one row. A length of a row can be substantially equal to a dimension of a component surface on which the ultrasonic probe array portion is traversing. The method can include inspecting the composite component for at least one of porosity, voids, damage, delamination, or presence of foreign objects based, in part, on the received response. The composite component can be an I-beam including a cap including an upper cap surface and a lower cap surface, a flange including an upper flange surface and a lower flange surface, the flange being separate from the cap, and a web that connects the cap and the flange, the web including a left web surface and a right web surface, and wherein traversing multiple ultrasonic probe array portions on the respective multiple component surfaces includes simultaneously traversing a first ultrasonic probe array portion on the upper cap surface, a second ultrasonic probe array portion on the upper flange surface, and a third ultrasonic probe array portion on the right web surface. Traversing the multiple ultrasonic probe array portions on the respective multiple component surfaces can include aligning the multiple ultrasonic probe array portions on the respective multiple component surfaces such that ultrasonic signal portions passed through the multiple ultrasonic probe array portions do not interfere with each other. The method can include recording the response to the ultrasonic signal received through the multiple ultrasonic probe array portions and analyzing the recorded response signal to inspect the composite component. Traversing the multiple ultrasonic probe array portions on the respective multiple component surfaces includes attaching the multiple ultrasonic probe array portions to a retaining member that includes at least one spring to retain the multiple ultrasonic probe array portions against the respective multiple component surfaces.

Certain aspects of the subject matter described here can be implemented as a method to inspect a composite component. The method includes simultaneously passing multiple ultrasonic signal portions through respective multiple component surfaces of the composite component, the multiple component surfaces being either separate from or at angles to each other. The method also includes receiving multiple response signals to the respective multiple ultrasonic signal portions from the multiple ultrasonic probe array portions and inspecting the composite component based, in part, on the multiple response signals.

This, and other aspects, can include one or more of the following features. Passing an ultrasonic signal portion through each component surface can include positioning an ultrasonic probe array portion on each component surface and traversing the ultrasonic probe array portion on each component surface while passing an ultrasonic signal portion through each component surface. Each ultrasonic probe array portion can include multiple ultrasonic probes arranged in a row that spans a length of each component surface. The method can include dividing an ultrasonic signal into multiple ultrasonic signals and aggregating the multiple response signals into a response to the ultrasonic signal. The method can include recording the response and analyzing the response to inspect the composite component. Inspecting the composite component can include inspecting the composite component for at least one of porosity, voids, damage, delamination or presence of foreign objects based, in part, on the multiple response signals.

Certain aspects of the subject matter described here can be implemented as a system for inspecting a composite component. The system includes an ultrasonic probe including multiple ultrasonic probe array portions to traverse respective multiple component surfaces of the composite component, wherein the multiple component surfaces are either separate from or at angles to each other. The system includes an ultrasonic signal generator to generate an ultrasonic signal to pass through the multiple ultrasonic probe array portions. The system also includes an ultrasonic signal receiver to receive multiple response signals to the ultrasonic signal from the multiple ultrasonic probe array portions. The system also includes an inspection unit to inspect the composite component based, in part, on the multiple response signals received by the ultrasonic signal receiver.

This, and other aspects, can include one or more of the following features. The inspection unit can include an encoder to detect a position of an ultrasonic probe array portion on a component surface of the composite component. The composite component can be a rotorcraft I-beam.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This disclosure relates to the inspection of components using ultrasonic techniques. In some cases, components are inspected for defects, e.g., prior to installation, during periodic maintenance, in response to failure or at other times. For example, components made of a composite material can have defects that are not obvious or are internal to the component, such as voids or cracking. The component can be inspected using ultrasonic techniques that can detect internal or unobvious defects. For example, the component can be inspected using an ultrasonic probe or ultrasonic probe array. Some components can be large or have multiple surfaces, and each component surface may need inspection. For example, a composite stiffener or stringer used in an aircraft can have multiple surfaces at different angles to each other. Inspecting a component by inspecting each component surface sequentially using a single probe or probe array can take a long duration. Furthermore, using different probes to inspect the different component surfaces can be problematic if a different ultrasonic signal is provided to each of the different probes. For example, the use of multiple probes can require a separate ultrasonic signal generator and signal receiver for each probe.

This disclosure describes a system for inspecting a component using an ultrasonic probe array. The inspection system can be used to inspect a component for defects such as porosity, voids, damage, cracks, corrosion, delamination, the presence of foreign objects, or other defects. The inspection system uses multiple portions of an ultrasonic probe array to inspect a component. A signal generator splits a single ultrasonic signal into multiple signal portions, and transmits each signal portion to a respective portion of the probe array. Each array portion is positioned at a separate surface of the component. Thus, multiple surfaces of the component are inspected simultaneously. The array portions can be traversed on each component surface while passing a respective ultrasonic signal portion through each component surface. In some cases, the inspection system is traversed along the component, and in some cases, the component is passed through the inspection system. When responses to the multiple signal portions are received, they are aggregated into a single response signal to the single ultrasonic signal. By inspecting multiple surfaces simultaneously, the process of inspecting the component is made more efficient, and the time to inspect a large part can be significantly reduced. The inspection system can also reduce fatigue or risk of injury for an operator, as fewer inspection passes may be needed. Furthermore, the inspection data can be recorded and saved for further analysis. Analyzing recorded inspection data can reduce the risk of escapes and improve the probability of detection.

Figure 1:
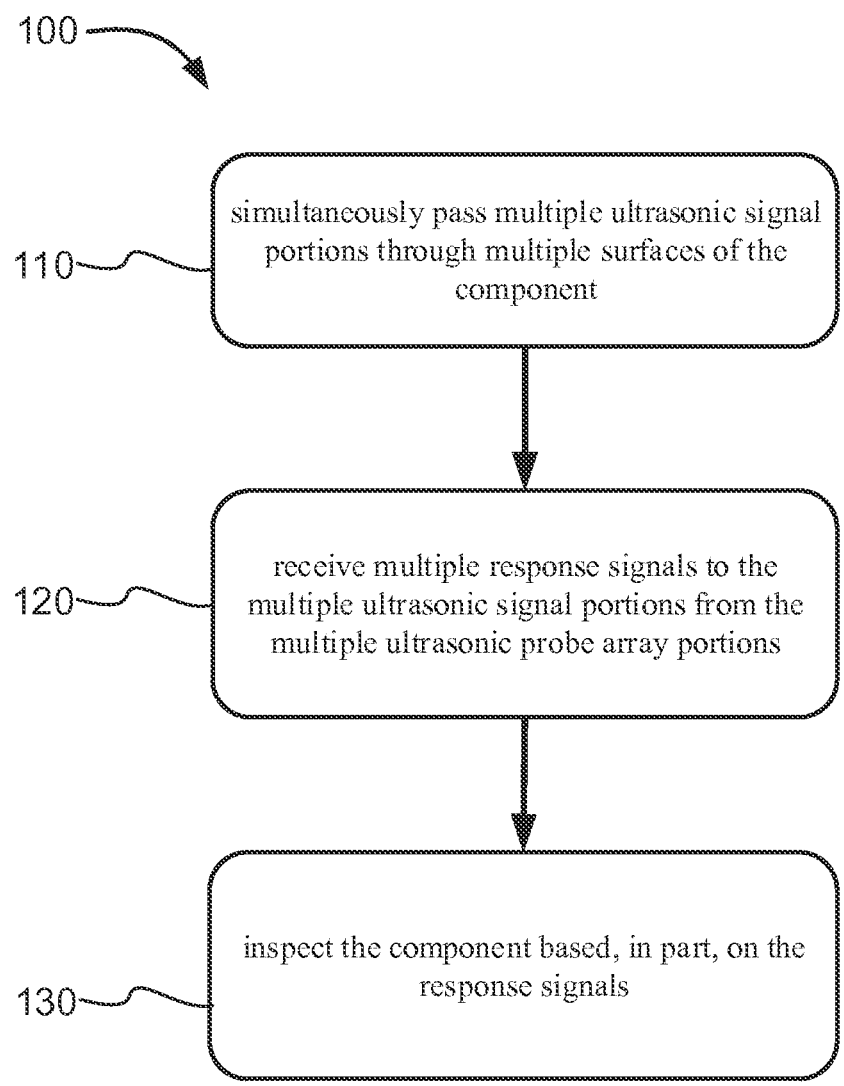
FIG. 1 shows a flowchart of an example inspection process for inspecting a component.
Figure 2:
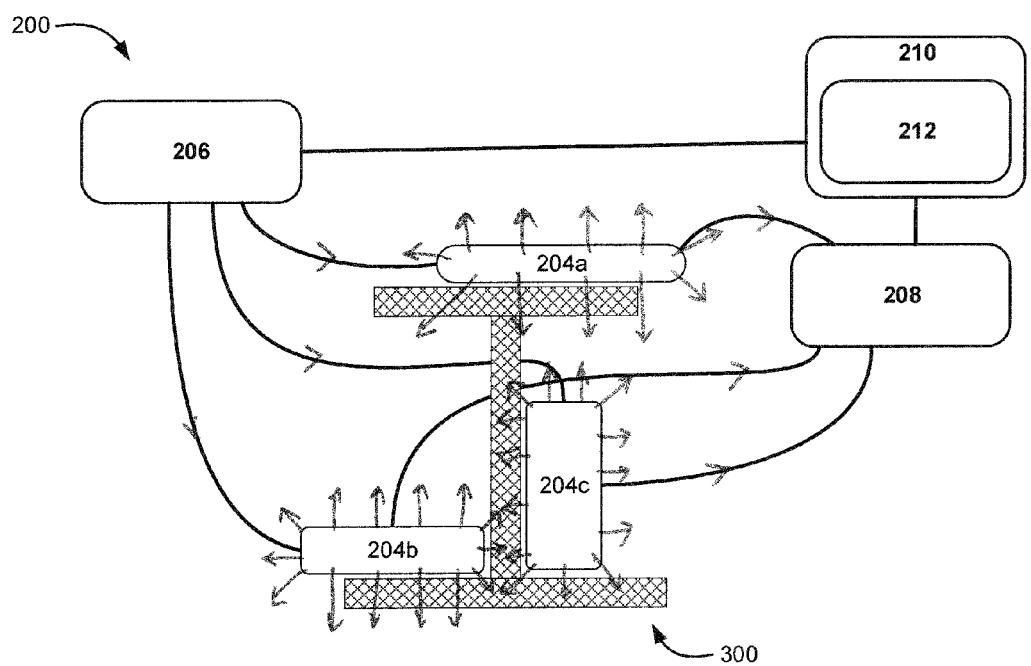
FIG. 2 shows a schematic of an example inspection system that can implement the inspection process.
Figure 3A:
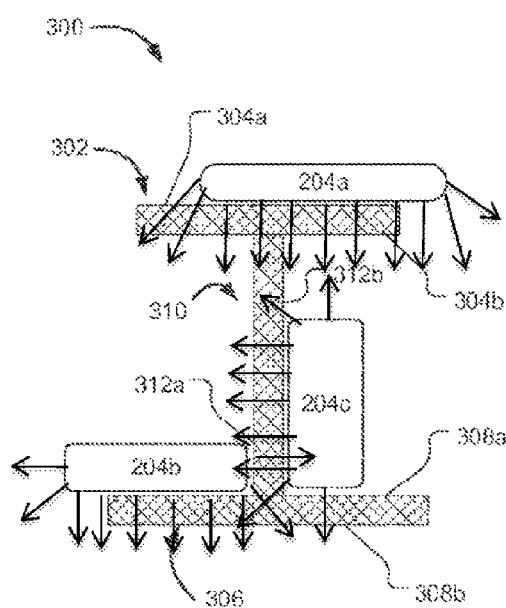
FIGS. 3A-3C are schematic diagrams showing examples of components.

FIG. 1 shows a flowchart of an example inspection process 100 for inspecting a component. At 110, multiple ultrasonic signal portions are simultaneously passed through multiple surfaces of the component. FIG. 2 shows a schematic of an example inspection system 200 that can implement inspection process 100. The inspection system 200 uses ultrasonic signals to inspect an example component 300. In FIG. 2, the example component 300 is a composite I-Beam, e.g., one used in a rotorcraft. FIG. 3A shows a schematic diagram of a cross section of example component 300. The component 300 includes a cap 302, a flange 306, and a web 310. The cap 302, flange 306, and web 310 can be formed as one piece or be formed separately and attached together (e.g. by bonding, adhesion, or another technique). A component like example component 300 can have component surfaces separate from or at angles to each other. For example the cap 302 includes an upper cap surface 304a and a lower cap surface 304b. The flange 306 includes an upper flange surface 308a and a lower flange surface 308b. The cap 302 and the flange 306 are connected by the web 310. The web 310 includes a left web surface 312a and a right web surface 312b. The array portions 204a-c can be positioned at one or more of these surfaces.

Figure 3B:
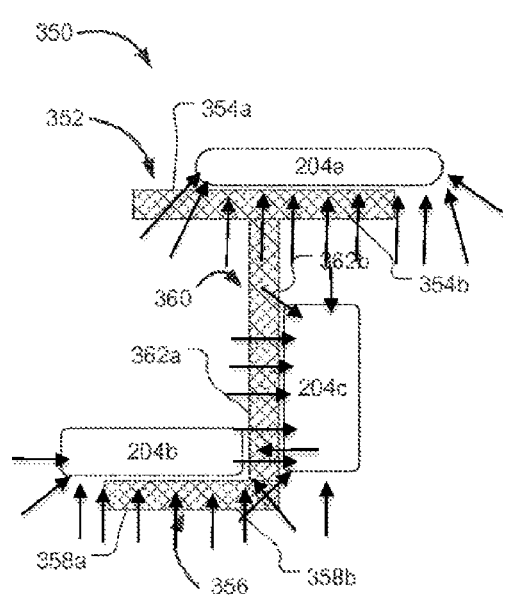

As another example component, FIG. 3B shows a schematic diagram of a component 350 having a J-beam shape. Component 350 includes a cap 352 with an upper cap surface 354a and a lower cap surface 354b. Component 350 also includes a web 360 with a left web surface 362a and right web surface 362b. Component 350 also includes a flange 356 with an upper flange surface 358a and a lower flange surface 358b. The array portions 204a-c can be positioned at these surfaces or on other surfaces of the component 350.

Components 300 and 350 are examples; the inspection process 100 can inspect components having a shape other than an I-beam shape or a J-beam shape, such as a C-channel shape, a T-shape, a tubular shape, a flat shape, an irregular shape, or another shape. Furthermore, the component can be made of a composite material, a metallic material, a plastic material, or another material or combination of materials. The component can also be a composite pultrusion, an aluminum extrustion, made of roll-formed steel, or made of forged steel, or made by another manufacturing process. The inspection process 100 could be used to inspect components used in aircraft applications such as fixed-wing aircraft, tiltrotor aircraft, rotorcraft, or other aircraft. The inspection process 100 could also be used to inspect components used in other applications such as automotive systems (e.g. automobiles, ATVs, motorcycles, or other automotive systems), submersible systems, marine systems (e.g. personal watercraft, boats, or other marine systems), agricultural systems (e.g. tractors or other agricultural systems), power equipment (e.g. generators, lawn mowers, or other power equipment), construction equipment (e.g. industrial vehicles, heavy machinery, or other equipment), transportation vehicles (e.g., railcars, locomotives, or other vehicles), or other systems.

The inspection system 200 includes an ultrasonic probe array 204 including multiple transducer elements arranged in a row or rows. The transducer elements are devices that send ultrasonic energy into the component 300 and receive ultrasonic energy from the component 300. For example, the transducer elements can be piezoelectric transducers or another type of transducer. In some cases, the transducer elements receive ultrasonic energy transmitted through the component 200 as in a through-transmission technique. In other cases, the transducer elements receive ultrasonic energy reflected from component surfaces or component defects as in a pulse-echo technique. In this manner, the transducer elements can be used to detect defects within the component 300. In some implementations, the transducer elements are in curved arrangements (e.g., concave, convex), in circular arrangements (e.g., an annular arrangement), in linear arrangements, in planar arrangements, or in arrangements of other shapes. Rigid or flexible transducer elements can be used.

The ultrasonic probe array 204 is divided into multiple array portions, e.g., a first array portion 204a, a second array portion 204b, a third array portion 204c. The array portions 204a-c are shown in example inspection positions at surfaces on the component 300. Three array portions 204a-c are shown in FIG. 2, though the array 204 can be divided into more or fewer array portions. The probe array 204 can be divided into multiple probe array portions. For example, the ultrasonic probe array 204 of 64 transducer elements can be divided into three separate portions of 32 elements in the first array portion 204a, 18 elements in the second array portion 204b, and 14 elements in the third array portion 204c. This is one example; a probe array can be divided into more or fewer array portions with any suitable number of transducer elements apiece. In some implementations, the probe array 204 is configured as a phased array ultrasonic probe.

An array portion can include a number of transducer elements such that the row of transducer elements spans a length substantially equal to or greater than a dimension of a surface of the component. For example, the length of the row of first array portion 204a can approximately equal or exceed a width of the upper cap surface 304a of the component 300. In some implementations, a user can replace one array portion with another array portion of a different size. For example, an array portion can be replaced by an array portion containing a larger number of transducer elements in order to inspect a wider component surface.

The array portions 204a-c can be positioned at one or more of the surfaces on component 300. For example, referring to FIG. 3, the first array portion 204a is positioned at the upper cap surface 304a to pass a first portion of the ultrasonic signal through the upper cap surface 304a, the second array portion 204b is positioned at the upper flange surface 308a to pass a second portion of the ultrasonic signal through the upper flange surface 308a, and the third array portion 204c is positioned at the right web surface 312b to pass a third portion of the ultrasonic signal through the right web surface 312b. The array portions 204a-c can also be positioned on other component surfaces not shown or labeled.

In some implementations, the ultrasonic probe array portions are attached to a retaining member (not shown) that includes at least one spring to retain the ultrasonic probe array portions against the respective component surfaces. In some implementations, the retaining member includes a mechanism such as an actuator, a scissoring mechanism, or another mechanism. The retaining member can maintain acoustic coupling between an array portion and a component surface. The retaining member can also maintain an array portion at a certain location as the array portion traverses the component. In this manner, a retaining member can improve inspection consistency and reduce operator fatigue.

Figure 3C:
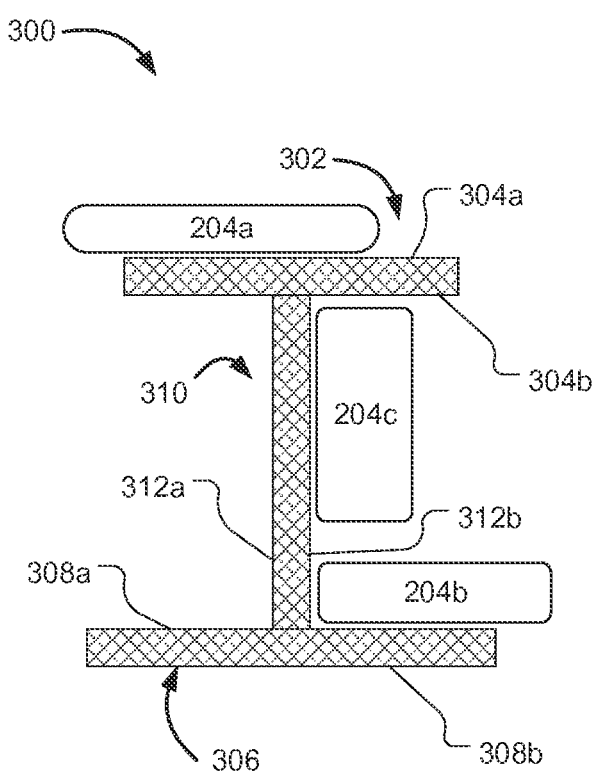

In some cases, the user can reposition the array portions 204a-c to other surfaces or to different locations on the same surface. As an example, FIG. 3C shows component 300 with array portions 204a-c positioned at different locations than shown in FIG. 3A. After an inspection, the user could reposition the first array portion 204a to a different location along the width of the upper cap surface 304a, as shown in FIG. 3C. The user could also, for example, reposition the third array portion 204c to the left web surface 312a or reposition the third array portion 204c to a different location on the right web surface 312b (as shown in FIG. 3C). Additionally, the second array portion 204b could be repositioned to the right side of the upper flange surface 308a, as shown in FIG. 3C. As another example, the third array portion 204c could be rotated 90° and shifted to reposition it at the lower cap surface 304b. In some implementations, one or more of the array portions 204a-c can be repositioned between inspection passes of the component 300. The ultrasonic probe array portions 204a-c can also be aligned or positioned on the respective component 300 surfaces such that the ultrasonic signal portions passed through the multiple ultrasonic probe array portions 204a-c do not interfere with each other.

The first array portion 204a, the second array portion 204b, and the third array portion 204c are coupled to a signal generator 206. The signal generator 206 transmits an ultrasonic signal to the array portions 204a-c. For example, the ultrasonic signal can be an analog signal, a digital signal, an amplified signal, an electronic signal, or other type of signal. The signal generator 206 can split a single ultrasonic signal into multiple ultrasonic signal portions and transmit the multiple ultrasonic signal portions to the array portions 204a-c. The array portions 204a-c pass the ultrasonic signal portions into the component surfaces. In some implementations, the signal generator 206 generates an electronic ultrasonic signal, and the array portions 204a-c pass portions of the ultrasonic signal into the component surfaces as an acoustic signal.

In response to the ultrasonic signals, the array portions 204a-c generate response signals. The response signals can be pulse-echo signals, through-transmission signals, or other types of ultrasonic signals. At 120, the multiple response signals are received, for example, by an ultrasonic signal receiver. The inspection system 200 includes an ultrasonic signal receiver 208 that is coupled to the array portions 204a-c and receives the response signals from the array portions 204a-c. The signal receiver 208 can aggregate the multiple signals from the array portions 204a-c into a single signal. As such, the signal receiver 208 receives a single response signal to the single ultrasonic signal generated by signal generator 206.

At 130, the component is inspected based, in part, on the response signals. For example, the component can be inspected using an inspection unit. The inspection system 200 includes an inspection unit 210 that is connected to the signal generator 206 and the signal receiver 206. The inspection unit 210 is used to inspect the component for defects based, in part, on the response signals from the array portions 204a-c. For example, the inspection unit 210 can analyze the aggregated response signal from the signal receiver 208 to determine if the received response signals indicate a defect in the component. In some implementations, the inspection unit 210 is included as part of another system, such as a computer system or other data processing apparatus.

The inspection unit 210 can include an encoder 212 that can detect the position of one or more of the array portions 204a-c on the surface of the component 300. For example, the encoder 212 can detect the position of the array portions 204a-c as the array portions 204a-c are traversed along the surfaces of the component 300.

Figure 4:
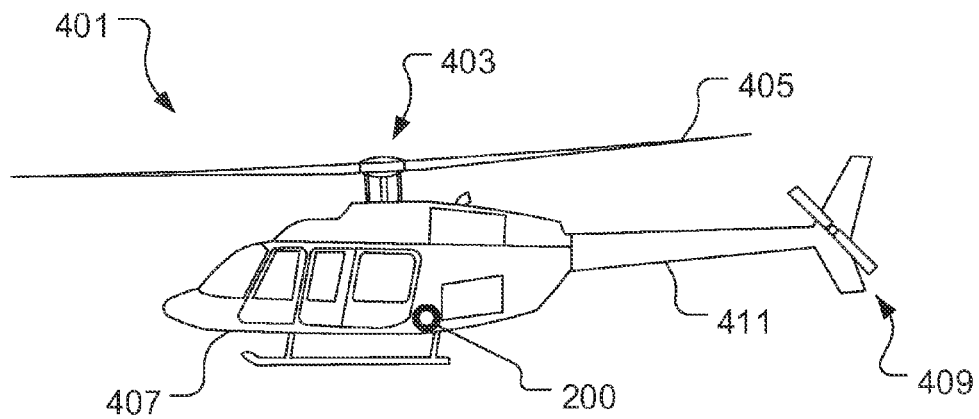
FIG. 4 is a schematic diagram showing an example of a rotorcraft.

In some implementations, the inspection system 200 records the response to the ultrasonic signal received through the ultrasonic probe array portions 204a-c. In some implementations, the data from the encoder 212 can be included with the recorded response. In this manner, data from the encoder 212 can be used to identify the location on the component 300 of defects or features detected by the inspection system 200. By identifying defect locations, further analysis of the defects could be performed. Recording the response signal can also allow the inspections of multiple components 300 to be compared. As such, manufacturing procedures, material compositions, etc. can be compared and improved based on the recorded signals. The inspection process 100 can be used to inspect parts for an aircraft. As an example, FIG. 4 shows a schematic diagram of an example rotorcraft 401. Rotorcraft 401 has a rotor system 403 with multiple rotor blades 405. Rotorcraft 401 can further include a fuselage 407, anti-torque system 409, and an empennage 411. The rotorcraft 401 can also include components 300 that can be inspected by inspection process 100. A component 300 is shown in an example location within the fuselage of the rotorcraft 401.

Figure 5:
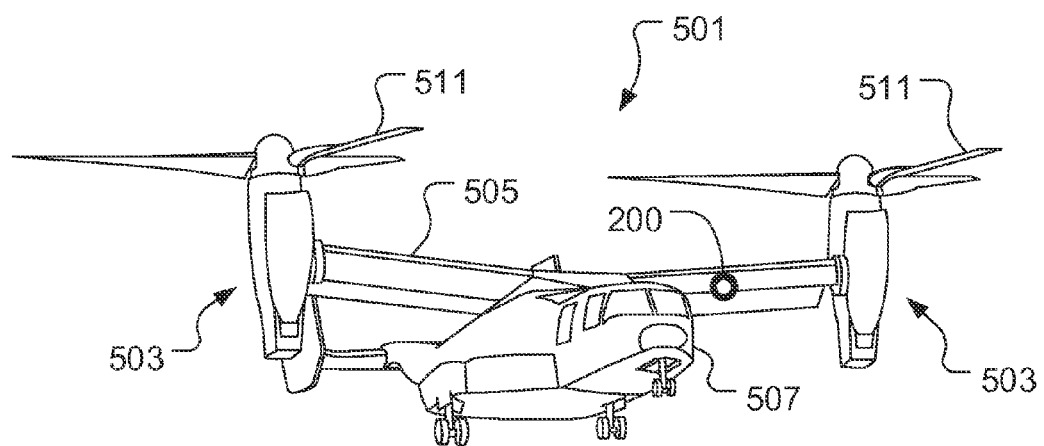
FIG. 5 is a schematic diagram showing an example of a tiltrotor aircraft.

As another example aircraft, FIG. 5 shows a schematic diagram of an example tiltrotor aircraft 501. Aircraft 501 includes a fuselage 507 with attached wings 505. Nacelles 503 are carried at the outboard ends of wings 505 and are rotatable between the helicopter-mode position shown and a forward-facing airplane-mode position (not shown). Nacelles 503 carry engines and transmissions for powering rotor systems 511 in rotation. An engine may be an internal combustion engine, an electrical power source and associated motor, or any other suitable technique for powering rotor system 511. The tiltrotor aircraft 501 can include components 200 that can be inspected by inspection process 100. A component 300 is shown in an example location within a wing of the tiltrotor aircraft 501.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results

What is claimed is:

1. A method to inspect a plurality of composite components of an aircraft, the method comprising:
    identifying the plurality of composite components of an aircraft in need of ultrasonic inspection;
    traversing a plurality of ultrasonic probe arrays capable of being repositioned in different configurations on surfaces of a first composite component of the aircraft, wherein the surfaces are either separate from or at angles to each other;
    simultaneously passing a plurality of ultrasonic signals into the plurality of component surfaces of the composite component by:
        generating a plurality of ultrasonic signals; and
        transmitting the plurality of ultrasonic signals through the composite components;
    detecting, using the plurality of ultrasonic probe arrays, ultrasonic signals that are transmitted through and reflected from the first composite component; and
    determining the position of the plurality of repositionable ultrasonic probe arrays with an encoder to identify the location of defects or features of the first composite components;
    repositioning the ultrasonic probe arrays into a new configuration on the surface of the aircraft to match a second composite component within the aircraft; and
    repeating the detection step to identify additional defects on the aircraft.

2. The method of claim 1, wherein receiving the response to the ultrasonic signal through the plurality of ultrasonic probe arrays comprises:
    receiving a plurality of response signals to the respective plurality of ultrasonic signals at the component surfaces, each response signal received from a respective composite component surface in response to a respective ultrasonic signal; and
    aggregating the plurality of response signals to form an image of component surface.

3. The method of claim 1, further comprising inspecting the first composite component for at least one of porosity, voids, damage, delamination, or presence of foreign objects based, in part, on the received response.

4. The method of claim 1, wherein the first composite component is an I-beam installed in an aircraft comprising a cap including an upper cap surface and a lower cap surface, a flange including an upper flange surface and a lower flange surface, the flange being separate from the cap, and a web that connects the cap and the flange, the web including a left web surface and a right web surface, and wherein traversing the plurality of ultrasonic probe arrays on the respective plurality of component surfaces comprises simultaneously traversing a first ultrasonic probe array on the upper cap surface, a second ultrasonic probe array on the upper flange surface, and a third ultrasonic probe array on the right web surface.

5. The method of claim 1, wherein traversing the plurality of ultrasonic probe arrays on the respective component surfaces comprises aligning the plurality of ultrasonic probe arrays on the respective plurality of component surfaces such that ultrasonic signals portions passed through the plurality of ultrasonic probe arrays do not interfere with each other.

6. The method of claim 1, further comprising: recording the response to the ultrasonic signal received through the plurality of ultrasonic probe arrays; and
    analyzing the recorded response signal to inspect the first composite component.

7. The method of claim 1, wherein traversing the plurality of ultrasonic probe arrays on the respective plurality of component surfaces comprises attaching the plurality of ultrasonic probe arrays to a retaining member that includes at least one spring to retain the plurality of ultrasonic probe arrays against the respective plurality of component surfaces.

8. A method to inspect a plurality of composite components of an aircraft, the method comprising:
    positioning a plurality of ultrasonic signal probe arrays configured to position in different configurations in contact with a surface of a first composite component of the aircraft;
    simultaneously transmitting a plurality of ultrasonic signals from the plurality of ultrasonic probe arrays through respective component surfaces of the composite component of the aircraft, the composite component surfaces being either separate from or at angles to each other;

receiving a plurality of response signals to the respective plurality of ultrasonic signals from the plurality of repositionable ultrasonic probe arrays, wherein the plurality of response signals includes ultrasonic signals transmitted through the composite component and ultrasonic signals reflected from surfaces of the composite component;

inspecting the composite component based, in part, on the plurality of response signals; and determining the position of the plurality of repositionable ultrasonic probe array transducers arrays with an encoder to identify the location of defects or features detected on the composite component;

repositioning the ultrasonic probe arrays into a new configuration on the surface of the aircraft to match a second composite component and repeating the detection step to identify additional defects of the aircraft.

9. The method of claim 8, wherein passing an ultrasonic signal through each component surface comprises:

positioning one of the plurality of ultrasonic probe arrays on each the respective component surface; and traversing the one of the plurality of ultrasonic probe arrays on each component surface while passing the ultrasonic signal portion through each component surface.

10. The method of claim 9, wherein each ultrasonic probe array comprises a plurality of ultrasonic transducers arranged in a row that spans a length of each the respective component surface.

11. The method of claim 8, further comprising: generating the plurality of ultrasonic signals; and aggregating the plurality of response signals into a an aggregate response signal.

12. The method of claim 11, further comprising: recording the aggregate response signal; and analyzing the aggregate response signal to inspect the respective composite component.

13. The method of claim 8, wherein inspecting the composite components comprises inspecting the composite components for at least one of porosity, voids, damage, delamination or presence of foreign objects based, in part, on the plurality of response signals.

14. A system for inspecting structurally different composite components of an aircraft, the system comprising:

a plurality of ultrasonic probe arrays capable of being repositioned in different configurations and operable to traverse surfaces of the structurally different composite components of the aircraft, wherein the surfaces are either separate from or at angles to each other adjacent to one or more parts of the aircraft, each of the plurality of ultrasonic probe arrays comprising:

an ultrasonic signal generator to generate a plurality of ultrasonic signals, wherein the plurality of signals pass through the composite components or reflected from the composite components of the aircraft;

an ultrasonic signal receiver to simultaneously receive a plurality of response signals, wherein the plurality of response signals include a plurality of ultrasonic signals transmitted through the composite components and a plurality of ultrasonic signals reflected from surfaces of the composite component;

a display unit that shows the composite components based, in part, on the plurality of response signals received by the ultrasonic signal receiver from ultrasonic signals transmitted through or reflected by the composite components of the aircraft; and an encoder connected to the plurality of ultrasonic probe arrays, wherein the encoder is capable of identifying the location of defects or features detected on the composite components.

15. The system of claim 14, wherein the display unit comprises the encoder to detect a position of an ultrasonic probe array on a component surface of the composite components.

16. The system of claim 14, wherein the one of the composite components is a rotorcraft I-beam.

17. The system of claim 14, wherein the display unit shows at least one of porosity, voids, damage, delamination, or presence of foreign objects in the composite components.

* * * * *